United States Patent [19]

Levitt et al.

[11] Patent Number: 4,628,056
[45] Date of Patent: Dec. 9, 1986

[54] NOVEL OXOPYRIMIDINE DERIVATIVES, PHARMACEUTICAL COMPOSITIONS CONTAINING THEM AND THEIR USE AS ANTICONVULSANT, ANTIANXIETY AND MUSCLE RELAXANT AGENTS

[75] Inventors: Barrie Levitt, Haifa; Morris Stolar, Tel Aviv, both of Israel

[73] Assignee: Taro Pharmaceutical Industries Ltd., Israel

[21] Appl. No.: 647,680

[22] Filed: Sep. 5, 1984

[30] Foreign Application Priority Data

Sep. 14, 1983 [IL] Israel ............................. 69722

[51] Int. Cl.$^4$ .................. A61K 31/515; C07D 239/62; C07D 239/64
[52] U.S. Cl. ..................................... 514/270; 514/906; 544/302; 544/303; 544/305
[58] Field of Search .................. 544/305, 302, 303; 424/254; 514/274, 270

[56] References Cited

U.S. PATENT DOCUMENTS 1,960,170  5/1933  Schnider ........................... 544/305
3,948,896  4/1976  Vida .................................. 424/254
4,046,894  9/1977  Samour et al. .................... 424/254

OTHER PUBLICATIONS

Raines et al., *Journal of Pharmacology and Exp. Ther.* vol. 186, No. 2, pp. 315–322, (1973).
Raines et al., *Epilepsia*, vol. 20, pp. 105–113, (1979).
Raines et al., *Epilepsia*, vol. 16, pp. 575–581, (1975).
Raines et al., *Chemical Abstracts*, 79:87539k, 1973.
Raines et al., *Chemical Abstracts*, 92:174402x, 1980.
Weinryb et al., *Chemical Abstracts*, 76:1206c, 1972.
Stavber et al., *Chemical Abstracts*, 99:157381s, 1983.
McElvain, *Journal of the American Chemical Society* vol. 57, pp. 1303–1304, 1935.
Samour et al., *Journal of Medicinal Chemistry*, vol. 14, pp. 187–189, 1971.

Primary Examiner—Donald G. Daus
Assistant Examiner—Stephen M. Kapner
Attorney, Agent, or Firm—Brumbaugh, Graves, Donohue & Raymond

[57] ABSTRACT

There are disclosed novel oxopyrimidine derivatives of the general formula

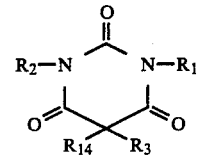

wherein $R_1$ and $R_2$ may be the same or different and are each hydrogen or lower alkyl optionally substituted by lower alkoxy, and $R_3$ and $R_4$ may be the same or different and are each phenyl optionally substituted by lower alkyl or halogen, provided that when $R_1$ and $R_2$ are both hydrogen, $R_3$ and $R_4$ are each substituted phenyl. Pharmaceutical compositions containing these compounds and their use as anticonvulsant, antianxiety and muscle relaxant agents are described.

10 Claims, No Drawings

NOVEL OXOPYRIMIDINE DERIVATIVES, PHARMACEUTICAL COMPOSITIONS CONTAINING THEM AND THEIR USE AS ANTICONVULSANT, ANTIANXIETY AND MUSCLE RELAXANT AGENTS

The present invention relates to novel oxopyrimidine derivatives which may also be named barbituric acid derivatives, to pharmaceutical compositions containing them and to methods of treating mammals for strain and stress conditions and nervous dysfunctions such as convulsions, seizure, muscle stiffness, nervous strain and anxiety.

Barbituric acid and its derivatives have been known since the turn of the century to possess pharmacological properties and some of them serve as active ingredients in widely used drugs. Barbituric acid derivatives are known to act mainly as sedatives, hypnotics and anaesthetics. Certain derivatives have also an anticonvulsive effect and are therefore employed in the treatment of epilepsy. Thus, pharmaceutical compositions containing 5-ethyl-5-phenyl barbituric acid (phenobarbital) are at present most widely used as drugs employed in the treatment of epilepsy. However, like other barbituric acid derivatives, phenobarbital has also sedative and hypnotic effects, which are a disadvantage in the treatment of epilepsy. Therefore, a great effort has been devoted to the search for compounds which have anticonvulsant properties and at the same time are devoid of sedative and hypnotic effects.

U.S. Pat. No. 4,046,894 discloses inter alia phenobarbitals which are substituted on both nitrogens by alkoxymethyl groups. The compounds have anticonvulsant properties and are also devoid of hypnotic effects. However, as illustrated in the above mentioned specification, the compounds have a relatively short term activity, with time of peak activity ranging between 1 to 2 hours and complete laps of activity after between 2 to 8 hours, depending on the substituent on the nitrogen ring.

Another known derivative of barbituric acid is the 5,5-diphenyl barbituric acid which was disclosed by S. M. McElvain in J. Am. Chem. Soc. 57, 1303 (1935). The compound was found to be effective only in very large doses and therefore no pharmacological application was suggested. Raines et al. reported in Epilepsia 20, 105 (1979) that 5,5-diphenyl barbituric acid has an anticonvulsant effect on rodents but with the disadvantage of relatively short term activity.

Prolonged activity is a valuable attribute of drugs in general and of anticonvulsant drugs in particular. Aside from allowing infrequent administration, it also improves patients' compliance with the drug. Furthermore, serum and tissue levels, which are crucial for maintaining therapeutic effectiveness, are more stable with a long acting compound. Moreover, stable serum levels reduce the incidence of break-through seizures and possible other adverse effects.

It is therefore the object of the present invention to provide novel barbituric acid derivatives having a long acting anticonvulsant, and/or muscle relaxant and/or tranquilizing activity and being at the same time devoid of any significant hypnotic and sedative effects.

A further object of the invention is to provide pharmaceutical compositions containing as active material the novel compounds of the invention.

A further object of the present invention is to provide novel methods for the treatment of convulsions, seizures, muscle stiffness, nervous stress or anxiety in mammals.

In accordance with the present invention there is provided a new barbituric acid derivative of the general formula I

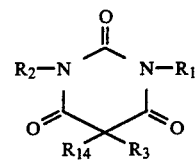

wherein $R_1$ and $R_2$ may be the same or different and are each hydrogen or lower alkyl optionally substituted by lower alkoxy, and $R_3$ and $R_4$ may be the same or different and are each phenyl optionally substituted by lower alkyl or halogen provided that when $R_1$ and $R_2$ are both hydrogen and $R_3$ and $R_4$ are each a substituted phenyl, and addition salts of such compounds.

When $R_3$ and $R_4$ are both unsubstituted phenyl $R_1$ and $R_2$ are preferably methoxymethyl or methyl.

The novel compounds of the invention are prepared by methods which are similar to known methods for the preparation of known barbituric acid derivatives.

Thus the 5,5-di-(substituted phenyl)-barbituric acids of the invention may be prepared by reacting aloxane with a substituted benzene in a manner similar to the preparation of diphenyl barbituric acid described by McElvain, loc. cit. In addition, the compounds in their free acid form are converted by techniques, well known to the chemist, into salts such as sodium or potassium salts.

A 1,3-bis(alkoxyalkyl)-5,5-di(optionally substituted)-phenylbarbituric acid according to the invention may be prepared by reacting a 5,5-di(optionally substituted)-phenyl barbituric acid with an alkali hydride to form the corresponding barbiturate salt which is then reacted with a haloalkyl alkyl ether in a process similar to that described by Samour et al., J. Med. Chem. 14, 187 (1971).

A 1,3-bis(alkyl)-5,5-di(optionally substituted)phenyl-barbituric acid according to the invention may be prepared by oxidizing 1,3-dialkyl barbituric acid to the corresponding 1,3-dialkyl aloxane, which is then reacted with optionally substituted benzene, in a similar way as mentioned above for aloxane (McElvain, loc. cit), to yield the desired product.

Examples of haloalkyl alkyl ethers suitable for use in the preparation of 1,3-bis(alkoxyalkyl) derivatives according to the invention are chloromethyl methyl ether, chloromethyl ethyl ether, chloromethyl propyl ether, chloromethyl butyl ether and chloromethyl phenyl ether.

Examples of substituted benzenes suitable for use in the preparation of the 5,5-di(substituted) phenyl derivatives according to the invention are toluene, ethylbenzene, propylbenzene, fluorobenzene, chlorobenzene, bromobenzene and iodobenzene.

The invention also provides for pharmaceutical compositions comprising as active material a compound of the above general formula I together with a pharmaceutically acceptable carrier.

The pharmaceutical compositions according to the invention may be in any conventional form such as solutions for injection, preparations for oral administration such as syrup, tablets, dragees or capsules or preparations for anal administration such as suppositories.

The invention also provides for a method of treatment of mammals suffering from convulsions, seizures, muscle stiffness, nervous strain or anxiety comprising administering to a patient an effective amount of a compound of the above general formula I.

The efficacy of the anticonvulsant activity of the compounds of the invention is demonstrated by tests studying the protection against a maximal electro shock seizure (MES) in rats treated with the compounds of the invention. MES tests are presently widely used for the assessment of anticonvulsant properties of chemical compounds, mainly due to the good correlation between the test results and the clinical finding of efficacy in patients suffering from epilepsy. In the MES tests carried out in order to evaluate the anticonvulsant properties of the invention, corneal electrodes were employed, the current was 150 milliamperes and a 60 hertz 200 milliseconds stimulus was applied. Rats were tested on the day prior to drug administration so as to eliminate from the study any animals failing to respond with a complete tonic convulsion including tonic hind-limb extension (THE), which serves as the basis for the assessment of the efficacy of the active material employed. Animals protected from THE, are regarded as protected in the MES tests.

The following are results of MES tests performed with 1,3-bis(methoxymethyl)5,5-diphenyl-barbiturate:

1,3-bis(methoxymethyl)-5,5-diphenylbarbiturate was dissolved in warm polyethylene glycol 400, and the solution administered in a dose of 500 mg/kg by stomach tube to 8 male, 120 gm, Sprague-Dawley rats. These animals were tested for maximum electro shock seizure (MES) at 6 and 23 hours after administration. All animals were previously demonstrated to exhibit a full maximal seizure to electrical stimulation.

The results obtained are summarized below:

| Dose | Number Protected/Number Injected and Tested after: | |
|---|---|---|
|  | 6 Hr | 23 Hr. |
| 500 mg/kg | *2/8 | **7/7 |

*An additional animal was protected but stimulus delivery may not have been complete.
**One animal died overnight, probably due to stomach perforation and thus only seven animals were available for study.

Thus, the compound is effective in the rat. The effect which is detectable at six hours, is most apparent at 23 hours. The protection against maximum electro-shock seizure was complete and therefore it is conceivable that the dose was excessive and that substantial protection would occur at much smaller doses. The protracted duration of action is a substantial advantage in antiepileptic drugs.

The non-toxicity of the compound was tested by repeated administration of a high dosage to same animals, as follows:

1,3-bis(methoxymethyl)-5,5-diphenylbarbiturate suspended in warm polyethylene glycol 400 was administered in a dose of 1500 mg/kg by gastric tube to six male, 100 g, Sprague Dawley rats. A dose of 1500 mg/kg was administered to same rats after 24 hours and again after 48 hours of first administration. Animals were examined for several hours after administration, again prior to the next dosing, and through additional 3 days after the last administration. No toxic effect was observed during the five days of the test. All animals continued to behave normally and no influence on locomotion, escape behavior, feeding or any other observable effect was detected.

The following are results of MES tests performed with 1,3-bis(methyl)-5,5-diphenylbarbiturate:

1,3-bis(methyl)-5,5-diphenylbarbiturate was suspended in polyethylene glycol 400 in a ratio of 60 mg/ml and dissolved by warming and stirring; the solution obtained was administered by means of a stomach tube in a dose of 500 mg/kg, to 15 rats of either sex. Rats were tested for MES at 1, 4, 8 and 24 hours after administration and the results obtained are summarized below:

| Dose | Number Protected/Number Injected and Tested after: | | | |
|---|---|---|---|---|
|  | 1 Hr | 4 Hrs | 8 Hrs | 24 Hrs |
| 500 mg/ml | 0/5(0%) | 1/5(20%) | 1/5(20%) | 8/15(53%) |

All animals tested were alert throughout the experiment and did not behave drugged. They had a normal escape behaviour pattern and there was no evidence of a neurological deficit. There was also no change in their food intake.

Thus, 1,3-bis(methyl)-5,5-diphenylbarbiturate have a very long time course of action with a long latency preceeding the onset of action. The dose administered approximated an $ED_{50}$ at the 24 hour test period. Therefore it is conceivable that a larger does would produce a greater degree of protection against electroshock seizures. It is also possible that a longer test period would have revealed a larger percentage of animals protected.

The following are the results of MES tests performed with 5,5-di(4-fluoro-phenyl)-barbituric acid:

5,5-di(4-fluoro-phenyl)-barbituric acid was dissolved in alkaline saline and administered by gastric tube in a dose of 250 mg/kg (volume 1.0 ml per rat) to nine male, 100 g, Sprague-Dawley rats. Four hours after drug administration, five animals were subjected to a maximal electoshock seizure test. At this time, three of these five rats were protected from a maximal tonic extensor seizure. At 20 hours after drug administration, all animals were tested. Of the four not previously shocked, three were protected; of the five that had been shocked 16 hours previously, all were protected. Thus, with an intragastric administration of 20 mg/kg, a 60% protection at 4 hours and about a 90% protection at 20 hours is achieved.

The tranquilizing and muscle relaxant properties of the compounds of the invention are demonstrated by the behavioural and motor effects observed with mice treated with the compounds of the invention. The following are results of tests performed with 5,5-diethylphenylbarbituric acid and 5,5-ditolylbarbituric acid:

5,5-Diethylphenylbarbituric acid in alkalinized saline was administered intraperitoneally to Swiss Webster mice. Six mice received 250 mg/kg of active material and 5 received 500 mg/kg. Within 30 minutes all the five mice which received the larger dose exhibited muscle hypotonia and little motor activity, appeared quieted and were prefectly capable of escape behaviour. The six mice receiving the 250 mg/kg exhibited a similar quieting effect about 2 hours after drug administration. No deaths occurred after the four hours observation period.

A solution of 5,5-ditolylbarbituric acid made by alkalinization with sodium hydroxide was administered intraperitoneally to mice. Eight mice received a dose of 200 mg/kg, subsequent to which they all exhibited low muscle tone and appeared quite, not exhibiting much spontaneous motor activity. Three mice received 300 mg/kg and exhibited moderate muscle flaccidity at 3 hours after injection.

The behavioural and motor effects observed in tested compounds are similar to those observed with centrally acting skeletal muscle relaxants and/or tranquilizing drugs. The combination of the tranquilizing effect without impairing the capacity of the animal to react to its environment is highly desirable in agents used for the treatment of anxiety.

Hypnotic activity or depression of the central nervous system was not exhibited by the compounds of the invention.

The invention is further illustrated by the following nonlimiting examples:

EXAMPLE 1

Preparation of 1,3-bis(methoxymethyl)-5,5-diphenyl barbiturate 5,5-Diphenylbarbituric acid (28.0 g, 0.1 mole) was dissolved in dimethylformamide (250 ml). To the cooled solution sodium hydride (4.8 g, 0.2 mole) was added and the mixture was stirred for 30 minutes. Chloromethyl methyl ether (17.7 g, 0.22 mole) was added to the mixture over a period of 30 minutes. The reaction mixture was stirred for 1 hour, then poured into ice-water (120 ml). The solid precipitate was filtered, washed with water and crystallized from ethanol.
m.p.: 134°–138° C.
Total yield: 70%.
Proton magnetic resonance frequencies in deuterated chloroform expressed as chemical shifts (δ) in ppm downfiled from tetramethylsilane (TMS):
7.2 ppm; multiplet; 10 aromatic protons.
5.3 ppm; singlet; 4 methylene protons.
3.3 ppm; singlet; 6 methyl protons.

EXAMPLE 2

Preparation of 1,3-bis(methyl)-5,5-diphenylbarbiturate

In a 500 cc. 3-necked flask fitted with a reflux condenser, a mercury seal stirrer and a thermometer in a well, were placed 18 g. of 1,3-dimethylalloxan monohydrate and 60 g. of sulfuric acid, sp. gr. 1.84. Then 75 cc. of benzene were added through the reflux condenser and the mixture heated in an oil-bath, with stirring, for four and one-half hours at 75°–80°. After this time the reaction mixture was cooled, most of the benzene layer decanted, and the sirupy sulfuric acid layer poured into 150 cc. of cold water. The precipitated material was filtered and washed in a beaker with 100 cc. of water and refiltered. After drying in a vacuum this material was chromatographed on silica to furnish the pure product.
m.p.: 206°–207° C.
Total yield: 60%

EXAMPLE 3

Preparation of 5,5-di(p-tolyl)-barbituric acid

In a 500 cc. 3-necked flask fitted with a reflux condenser, a mercury seal stirrer and a thermometer in a well, were placed 16 g. of alloxan monohydrate and 60 g. of sulfuric acid, sp.gr. 1.84. Then 75 cc. of toluene were added through the reflux condenser and the mixture heated in an oil-bath, with stirring for four and one-half hours at 75°–80°. After this time the reaction mixture was cooled, most of the toluene later decanted, and the sirupy sulfuric acid later poured into 150 cc. of cold water. The precipitated material was filtered and washed in a beaker with 100 cc. of water and refiltered. After drying in a vacuum this material was dissolved in 160 cc. of boiling glacial acetic acid, filtered and allowed to crystallize.

After filtration, washing with water and ether the crystallized material was chromatographed on silica to furnish the pure product.
m.p.: 275°–278° C.
Proton magnetc resonance frequencies in DMSO expressed as chemical shifts downfiled from TMS:
2.32 ppm; (s, 6 methyl protons).
7.15 ppm; (dd, 8 aromatic protons).
11.68 ppm; (br s, 2NH protons).

EXAMPLE 4

Preparation of 5,5-diethylphenylbarbituric acid

Aloxane monohydrate was reacted with ethyl benzene in the presence of sulfuric acid in a process similar to the process for the preparation of 5,5-di(p-tolyl)-barbituric acid described above.

EXAMPLE 5

Preparation of 5,5-di-(4-fluorophenyl)-barbituric acid

In a 500 ml 3-necked flask fitted with a reflux condenser, a stirrer and a thermometer, were placed 16 g (0.1 mol) of alloxan monohydrate and 60 g of sulfuric acid (specific gravity 1.84). Then 96 g (1 mol) of fluorobenzene were added and the mixture heated in an oil-bath, with stirring for 4½ hours, at 85°. After this time the reaction mixture was cooled, most of the fluorobenzene later decanted, and the sirupy sulfuric acid layer poured into 150 ml of ice water. The precipitated material was filtered off, washed in a beaker with 100 ml of water and refiltered. After drying in a vacuum desicator this material was recrystallized from glacial acetic acid and yielded a product with melting point of 315°–318°. Plate chromatography over silica gel yielded a pure product.
m.p.: 327°–329° C.
Proton magnetic resonance frequencies in deuterated chloroform expressed as chemical shifts downfield from TMS:
7.3 ppm (dd, 4 aromatic protons).
11.8 ppm (br s, 2NH protons).

We claim:
1. A compound of formula I:

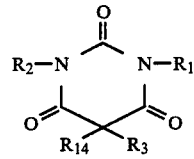

wherein $R_1$ and $R_2$ may be the same or different and are each hydrogen or lower alkyl optionally substituted by lower alkoxy, and $R_3$ and $R_4$ may be the same or different and are each phenyl, phenyl substituted by lower alkyl or phenyl substituted by halogen provided that when $R_1$ and $R_2$ are both hydrogen $R_3$ and $R_4$ are each a substituted phenyl; and addition salts thereof.

2. A compound according to claim 1 wherein $R_1$ and $R_2$ are both methoxymethyl and $R_3$ and $R_4$ are both phenyl.

3. A compound according to claim 1 wherein $R_1$ and $R_2$ are both methyl and $R_3$ and $R_4$ are both phenyl.

4. A compound according to claim 1 wherein $R_1$ and $R_2$ are both hydrogen and $R_3$ and $R_4$ are both tolyl.

5. A compound according to claim 1 wherein $R_3$ and $R_4$ are both ethylphenyl.

6. A compound according to claim 1 wherein $R_1$ and $R_2$ are both hydrogen and $R_3$ and $R_4$ are both fluorophenyl.

7. A pharmaceutical composition comprising as active material a compound of the general formula I as defined in claim 1 together with a pharmaceutically acceptable carrier.

8. A method of treating convulsion in mammals comprising administering to a patient an effective amount of a compound of the general formula I as defined in claim 1.

9. A method of effecting muscle relaxation in mammals comprising administering to a patient an effective amount of a compound of the general formula I as defined in claim I.

10. A method of treating anxiety in mammals comprising administering to mammals an effective amount of a compound of the general formula I as defined in claim 1.

* * * * *

UNITED STATES PATENT AND TRADEMARK OFFICE
CERTIFICATE OF CORRECTION

PATENT NO. : 4,628,056

DATED : December 9, 1986

INVENTOR(S) : Barrie LEVITT; Morris STOLAR

It is certified that error appears in the above-identified patent and that said Letters Patent is hereby corrected as shown below:

Col. 1, line 40, "laps" should read -- lapse --.

Col. 2, line 15, that portion of the formula reading "$R_{14}$" should read -- $R_4$ --;

Col. 2, line 22, after "hydrogen" delete "and";

Col. 4, line 32, "does" should read -- dose --;

Col. 4, line 45, "electoshock" should read -- electroshock --;

Col. 5, line 7, "quite" should read -- quiet --;

Col. 6, line 51, "downfield" should read -- downfiled --;

Col. 6, line 60, that portion of the formula reading "$R_{14} \diagdown R_3$" should read -- $R_3 \diagdown R_4$ --.

Signed and Sealed this

Twenty-eighth Day of April, 1987

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,628,056
DATED : December 9, 1986
INVENTOR(S) : Barrie Levitt et al It is certified that error appears in the above-indentified patent and that said Letters Patent is hereby corrected as shown below:

In the structural formula of the Abstract, "$R_{14}$" should read --$R_4$--.

Signed and Sealed this

Eighteenth Day of October, 1994

Attest:

BRUCE LEHMAN

Attesting Officer     Commissioner of Patents and Trademarks